US006451326B2

(12) United States Patent
Ensley

(10) Patent No.: US 6,451,326 B2
(45) Date of Patent: *Sep. 17, 2002

(54) COSMETIC COMPOSITIONS

(76) Inventor: Burt D. Ensley, 7 Colts Neck Dr., Newtown, PA (US) 18940

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/037,193

(22) Filed: Mar. 9, 1998

Related U.S. Application Data

(63) Continuation-in-part of application No. 08/641,627, filed on May 2, 1996, now Pat. No. 5,726,040.

(51) Int. Cl.⁷ ............................. A61K 6/00; A61K 7/42; A61K 7/035; A61K 31/74; C12P 21/06
(52) U.S. Cl. ........................... 424/401; 424/59; 424/69; 424/78.03; 435/69.1; 514/2; 514/12; 530/350
(58) Field of Search ............................. 435/69.1, 252.3, 435/252.33; 514/2, 773, 12; 424/401, 59, 69, 78.03; 530/323, 350

(56) References Cited

U.S. PATENT DOCUMENTS

| | | |
|---|---|---|
| 2,827,419 A | 3/1958 | Tourtellote |
| 3,393,080 A | 7/1968 | Erdi et al. |
| 3,632,350 A | 1/1972 | Battista |
| 3,839,590 A | 10/1974 | Battista |
| 3,887,703 A | 6/1975 | Manoussos et al. |
| 3,954,725 A | 5/1976 | Johnson et al. |
| 3,991,184 A | 11/1976 | Kludas et al. |
| 4,007,266 A | 2/1977 | Choay |
| 4,042,457 A | 8/1977 | Kuettner et al. |
| 4,108,849 A | 8/1978 | Thomas |
| 4,141,973 A | 2/1979 | Balazs |
| 4,186,188 A | 1/1980 | Gumprecht |
| RE30,239 E | 3/1980 | Kuettner et al. |
| 4,228,153 A | 10/1980 | Burov et al. |
| 4,293,099 A | 10/1981 | Berrebi et al. |
| 4,327,078 A | 4/1982 | Charlet et al. |
| 4,363,760 A | 12/1982 | Cioca |
| 4,389,487 A | 6/1983 | Ries |
| 4,419,288 A | 12/1983 | Cioca |
| 4,420,339 A | 12/1983 | Kato |
| 4,448,718 A | 5/1984 | Yannas et al. |
| 4,451,397 A | 5/1984 | Huc et al. |
| 4,454,159 A | 6/1984 | Musher |
| 4,464,362 A | 8/1984 | Kludas et al. |
| 4,474,763 A | 10/1984 | Lubowe |
| 4,474,851 A | 10/1984 | Urry |
| 4,488,911 A | 12/1984 | Luck et al. |
| 4,511,653 A | 4/1985 | Play et al. |
| 4,642,292 A | 2/1987 | Reid et al. |
| 4,659,740 A | * 4/1987 | Usher ........................ 514/773 |
| 4,664,110 A | 5/1987 | Schanzlin |
| 4,696,813 A | 9/1987 | Higa |
| 4,736,024 A | 4/1988 | Della Valle et al. |
| 4,783,523 A | * 11/1988 | Urry ........................... 530/323 |
| 4,820,642 A | 4/1989 | Edman et al. |
| 4,898,926 A | 2/1990 | Urry |
| 4,945,050 A | 7/1990 | Sanford et al. |
| 5,030,719 A | 7/1991 | Umemoto et al. |
| 5,055,298 A | * 10/1991 | Kludas ........................ 424/401 |
| 5,064,430 A | 11/1991 | Urry |
| 5,089,406 A | 2/1992 | Williams et al. |
| 5,726,040 A | 3/1998 | Ensley et al. |

FOREIGN PATENT DOCUMENTS

| | | |
|---|---|---|
| EP | 0128706 | 12/1984 |
| EP | 0154447 | 9/1985 |
| JP | 63-14707 | * 1/1998 |
| WO | WO 89/05137 | 6/1989 |

OTHER PUBLICATIONS

Fazio et al., Laboratory Investigations, vol. 58, pp 270–277.*
"Expression of Heterologous Proteins in *Escherichia coli*" *Methods in Enzymology* (185):Section II, 11–195, 1987.
"Heterologous Gene Expression in Yeast" *Methods in Enzymology* (185):Section IV, 231–482, 1987.
"Expression of Heterologous Genes in Mammalian Cells" *Methods in Enzymology* (185):Section V, 485–596, 1987.
Barrineau, et al., "Differential Expression of Aortic and Lung Elastin Genes During Chick Embryogenesis" *Dev. Biology* 87:46–51, 1981.
Brinster, et al., "Factors Affecting the Efficiency of Introducing Foreign DNA Into Mice by Microinjecting Eggs" *Proc. Nat. Acad. Sci. USA* 82:4438, 1985.
Chu, et al., "Cloning and Characterization of Five Overlapping cDNAs Specific for the Human proα1(I) Collagen Chain" *Nucleic Acids Res.* 10:5925–5934, 1982.
Devare, et al., "Expression of the PDGF–Related TRansforming Protein of Simian Sarcoma Virus in *E. Coli*" *Cell* 36:43–49, 1984.
Fazio, et al., "Cloning of Full–Length Elastin cDNAs From a Human Skin Fibroblast Recombinant cDNA Library: Further Elucidation of Alternative Splicing Utilizing Exon–Specific Oligonucleotides" *J. Invest. Dermatol.* 91(5):458–464, 1988.

(List continued on next page.)

*Primary Examiner*—W. Gary Jones
*Assistant Examiner*—Jehanne Souaya
(74) *Attorney, Agent, or Firm*—Choate, Hall & Stewart; Brenda Herschbach Jarre

(57) ABSTRACT

A cosmetic composition including a non naturally-occurring extracellular matrix protein in combination with a cosmetic carrier is described. The protein is preferably of human origin and has not been previously cross-linked. The protein is most preferably selected from the group consisting of soluble human procollagen and soluble human tropoelastin. Preferably, the composition contains at least two allelic variants of the protein, most preferably in substantially the same ratio at which they are found in epidermis of a selected individual. The individual may be selected, for example, on the basis of having youthful-appearing skin, of being the future wearer of the composition, or of other reasons.

9 Claims, No Drawings

OTHER PUBLICATIONS

Fazio, et al., "Isolation and Characterization of Human Elastin cDNAs, and Age–Associated Variation in Elastin Gene Expression in Cultured Skin Fibroblasts" *Lab. Invest.*, 58(3):270–277, 1988.

Ferguson, et al., "Cell–Surface Anchoring of Proteins Via Glycosyl–Phosphatidylinositol Structures" *Ann. Rev. Biochem.* 57:285–320, 1988.

Goldberger, et al., "The Reversible Masking of Amino Groups in Ribonuclease and Its Possible Usefulness in the Synthesis of the Protein" *Biochem* 1(3):401–405, 1962.

Gross, et al., "Selective Cleavage of the Methionyl Peptide Bonds in Ribonuclease with Cyanogen Bromide" *J. Am. Chem. Soc.* 83:1510–1511, 1961.

Gubler, et al., "A Simple and Very Efficient Method For Generating cDNA Libraries" *Gene* 25:263–269, 1983.

Hammer, et al., "Spontaneous Inflammatory Disease in Transgenic Rats Expressing HLA–B27 and Human $\beta_2$m: An Animal Model of HLA–B27–Associated Human Disorders" *Cell* 63:1099–1112, 1990.

Hutchinson, et al., "Mutagenesis at a Specific Position in a DNA Sequence" *J. Biol. Chem.* 253(18):6551–6560, 1978.

Hynes, et al., "Isolation and Analysis of cDNA and Genomic Clones of Fibronectin and its Receptor" *Methods in Enzymology* 144:447–463, 1987.

Indik, et al., "Alternative Splicing of Human Elastin mRNA Indicated by Sequence Analysis of Cloned Genomic and Complementary DNA" *Proc. Nat. Acad. Sci. USA* 84:5680–5684, 1987.

Indik, et al., "Production of Recombinant Human Tropoelastin: Characterization and Demonstration of Immunologic and Chemotactic Activity" *Arch. Biochim. Biophys.* 280(1):80–86, 1990.

Indik et al., "Structure of the 3' Region of the Human Elastin Gene: Great Abundance of Alu Repetitive Sequences and Few Coding Sequences" *Connect. Tissue Res.* 16:197–211, 1987.

Joyner, et al., "Production of a Mutation in Mouse En–2 Gene by Homologous Recombination in Embryonic Stem Cells" *Nature* 338:153–156, 1989.

Kornblihtt, et al., "Primary Structure of Human Fibronectin: Differential Splicing May Generate at Least 10 Polypeptides From a Single Gene" *EMBO J.* 4:1755–1759, 1985.

Mateeucci, et al., "Synthesis of Deoxyoligonucleotides on a Polymer Support" *J. Am. Chem. Soc.* 103(11):3185–3191, 1981.

Merrifield, "New Approaches to the Chemical Synthesis of Peptides" *Recent Prog. Hormone Res.* 23:451–482, 1967.

Miller, et al., "The Collagens: An Overview and Update" *Methods in Enzymology* (144):3–41, 1987.

Myers, et al., "Cloning a cDNA for the pro–α2 Chain of Human Type I Collagen" *Proc. Natl. Acad. Sci. USA* 78(6):3516–3520, 1981.

Palmiter, et al., "Dramatic Growth of Mice That Develop From Eggs Microinjected With Metallothionein–Growth Hormone Fusion Genes" *Nature* 300:611–615, 1982.

Pursel, et al., "Genetic Engineering of Livestock" *Science* 244:1281–1286, 1989.

Ramakrishnan, et al., "Comparison of the Selective Cytotoxic Effects of Immunotoxins Containing Ricin A Chain or Pokeweek Antiviral Protein and Anti–Thy 1.1 Monoclonal Antibodies" *Caner Res.* 44:201–208, 1984.

Rosenbloom, et al., "Extracellular Matrix 4: The Elastic Fiber" *FASEB J.* 7:1208–1218, 1993.

Rosenbloom, et al., "Biology of Disease Elastin: Relation of Protein and Gene Structure to Disease" *Lab. Invest.* 51(6):605–623, 1984.

Rupp, et al., "Structure and Expression of a Rat Agrin" *Neuron* 6:811–823, 1991.

Witkop, "Nonenzymatic Methods For the Preferential and Selective Cleavage and Modification of Proteins" *Adv. Protein Chem.* 16:221–321, 1961.

Wrenn, et al., "Identification of Multiple Tropoelastins Secreted by Bovine Cells" *Biol. Chem.* 262(5):2244–2249, 1987.

Young, et al., *Proc. Natl. Acad. Sci. USA* 80:6105, 1983.

Barlow, et al., "Molecular Cloning of Laminin" *Methods in Enzymology* 144:464–474, 1987.

Capecchi, "Altering the Genome by Homologous Recombination" *Science* 244:1288–1292 1989.

Hawley, D.K., et al., "Compilation and Analysis of *Escherichia coli* Promoter DNA Sequences" *Nucl. Acids Res.* 11(8):2237–2255, 1983.

Houdebine, et al., "Transgenesis in fish" *Experientia* 47(9):891–897, 1991.

Jansen, et al., "Immunotoxins: Hybrid Molecules Combining High Specificity and potent Cytotoxicity" *Immuno. Rev.* 62:185–216, 1982.

Kagan, et al., *Chemical Abs.* 85:15705n, 1976.

Killen, et al., "Specific Killing of Lymphocytes That Cause Experimental Autoimmune Myasthenia Gravis By Ricin Toxin–Acetylcholine Receptor Conjugates" *J. Immunol.* 133(5):2549–2553, 1984.

Lindley, "A New Synthetic Substrate for Trypsin and its Application to the Determination of the Amino–Acid Sequence of Proteins" *Nature* 178:647–648, 1956.

Mecham, "Elastin Synthesis and Fiber Assembly" *Annal. Ny Acad. Sci.* 624:137–146, 1991.

Ruoslahti, et al., "Fibronectin: Purification, Immunochemical Properties, and Biological Activities" *Methods in Enzymology*1982; 82 Pt. A:803–831.

Sanger, et al., "DNA Sequencing With Chain–Terminating Inhibitors" *Proc. Natl. Acad. Sci. USA* 74(12):5463–5467, 1977.

Shuman, "Production of transgenic birds" *Experientia* 47(9):897–905, 1991.

* cited by examiner

COSMETIC COMPOSITIONS

The present application is a Continuation-in-part of application Ser. No. 08/641,627, filed May 2, 1996, issued as U.S. Pat. No. 5,726,040 on Mar. 10, 1998.

BACKGROUND OF THE INVENTION

The human skin consists of two layers; a superficial layer called the epidermis that is epithelial tissue, and a deeper layer called the dermis that consists essentially of connective tissue. These two layers are bound together to form skin, which varies in thickness from less than about 0.5 mm, to 3 or even 4 millimeters. Exposure of the skin to sun, wind, and other factors leads to skin ageing, i.e., loss of moisture in the epidermal layers of the skin, resulting in loss of elasticity, skin tone and texture as degradation of certain proteins present in the skin takes place.

The connective tissue found in skin is essentially an intricate meshwork of interacting, extracellular molecules that constitute the so-called "extracellular matrix". The extracellular matrix includes proteins that are secreted locally and are widely distributed. The main types of proteins that make up the matrix include collagens, elastin, fibronectin and laminin.

Collagens are a family of highly characteristic fibrous proteins found in all multicellular animals. They are the most abundant proteins in mammals, constituting about 25 percent of their total protein. A central feature of all collagen molecules is their stiff, triple-stranded helical structure. See, for example, Miller and Gay, "The Collagens: An Overview and Update," pp. 3–41, *Methods in Enzymology* (ed. Colowick and Kaplan), v. 144 (1987), Academic Press, Inc.

Elastin, present in elastic fibers of tissues such as blood vessels and skin, gives these tissues the required ability to recoil after transient stretch. Elastin is the major component of these elastic fibers, where it is present as an extensively cross-linked polypeptide having a peculiar chemical composition. Approximately one third of the amino acids in elastin are glycine, 10–13 percent are proline, and over 40 percent are other amino acids with hydrophobic side chains. Elastin contains very small amounts of hydrophilic amino acids.

Laminin is a large glycoprotein and a major component of basement membranes. Laminin is made by all epithelial cells that have been studied. Laminin is made up of three different subunits disulfide-bonded into an asymmetric cross-linked structure. For review see Barlow et al., "Molecular Cloning of Laminin," pp. 404–474 in *Methods in Enzymology*, v. 144 (1987) Academic Press, Inc.

Fibronectin is a cell-surface and blood glycoprotein involved in a variety of cell surface phenomena. It is present as an insoluble form at the cell surface and in connective tissue, and found in soluble form in plasma. For reviews, see Ruoslahti et al., "Fibronectin: Purification, Immunochemical Properties, and Biological Activities," pp. 803–831, in *Methods in Enzymology*, supra; Hynes et al., "Isolation and Analysis of cDNA and Genomic Clones of Fibronectin and its Receptor," pp. 447–463, in *Methods in Enzymology*, v. 144, Academic Press, Inc. (1987).

Combinations of components of the extracellular matrix are often incorporated into cosmetic compositions. Elastin, in particular, is often utilized. Because the naturally-occurring crosslinked elastin fibers are insoluble (i.e., insoluble in water, organic solvents, and physiological fluids such as saline, blood, and lymph), the elastin is first rendered soluble using a variety of chemical and enzymatic methods. The rationale behind these procedures is that soluble elastin, and various derivatives thereof, is expected to penetrate into the skin to a greater degree than cross-linked elastin, compensating for loss of elastin during skin ageing. The chemical and enzymatic methods designed to solubilize elastin are problematic, however, because they can induce chemical and structural changes in the elastin molecule itself.

A further consideration when using proteins of the extracellular matrix in cosmetics concerns the degree to which the proteins produce unwanted allergic responses in the subject's skin. Such responses are of particular concern with compositions utilizing elastin since many cosmetics employ solubilized elastin isolated from the neck tendons of young calves or other non-human mammals.

There remains a need for the development of improved strategies, methods, and compositions that allow use of extracellular matrix proteins, particularly human proteins, in cosmetic compositions.

SUMMARY OF THE INVENTION

The present invention pertains to a cosmetic composition including a non naturally-occurring extracellular matrix protein in combination with a cosmetic carrier. The extracellular matrix protein is preferably of human origin and has not been previously cross-linked. The protein is most preferably selected from the group consisting of soluble human procollagen and soluble human tropoelastin. The extracellular matrix protein may include at least one additional non-naturally occurring amino acid sequence moiety, the amino acid sequence moiety selected from the group consisting of a hydrophobic sequence, a hydrophilic sequence, and a lysine-rich sequence.

In preferred embodiments of the present invention, the cosmetic composition is formulated to reproduce one or more aspects of the extracellular matrix found in skin of a selected individual. In particular, one aspect of the present invention involves the recognition that different individuals may produce different allelic variants, or populations of allelic variants of extracellular matrix proteins in their skin. As used herein, the term "allelic variants" refers to different versions of a protein, or a gene encoding that protein, present in the human population. Protein variants can differ from one another by addition, substitution, or deletion of one or more amino acids. Typically, such proteins are produced from gene variants that differ from one another by addition, substitution, or deletion of one or more nucleotides[1]. Alternatively or additionally, such protein variants can be produced by alternative splicing or other processing of genetic sequences.

According to one particularly preferred embodiment of the present invention, a particular individual is selected on the basis of having appealing skin characteristics. The allelic composition of one or more extracellular matrix proteins in that person's skin is identified, and that composition is reproduced in a cosmetic formulation. Those of ordinary skill in the art will recognize that what constitutes "appealing" skin may vary according to the preferences of the manufacturer of the cosmetic or the person onto whom the cosmetic is to be applied, and according to the circumstances under which the cosmetic is to be used. For example, in some contexts, skin is "appealing" if it has attributes characteristic of the skin of an individual who is chronologically younger than the posessor of the skin. In other contexts, skin is "appealing" if it has attributes similar or identical to those of the person to whom the cosmetic is to be applied, so that negative immune reactions can be minimized or avoided.

DETAILED DESCRIPTION OF CERTAIN PREFERRED EMBODIMENTS OF THE INVENTION

Definitions

One aspect of the invention is a cosmetic composition containing a non naturally-occurring form of an extracellular matrix protein. The following definitions clarify the scope of this and other aspects of the invention:

The term "cosmetic" or "cosmetic composition" as used herein, is intended to include any type of product that is applied in any manner directly to the person.

The term "extracellular matrix protein" refers to those macromolecules that constitute the extracellular matrix. The main classes of protein that make up the extracellular matrix are collagens, elastin, fibronectin, and laminin.

"Non naturally-occurring", when applied to the extracellular matrix proteins of the present invention means polypeptides: (i) produced from nucleic acids that were prepared using recombinant DNA methods; (ii); synthesized by, for example, chemical synthetic methods; (iii) separated from at least some of the biological materials with which the proteins are normally associated in nature, and purified using protein analytical procedures; (iv) associated with chemical moieties (e.g., polypeptides, carbohydrates, fatty acids, organic molecules, and the like) other than those associated with the polypeptide in its naturally-occurring state; or (v) that do not occur in nature.

"Non naturally-occurring", when applied to the nucleotide sequences encoding the extracellular matrix proteins of the present invention means a portion of genomic nucleic acid, cDNA, or synthetic nucleic acid which, by virtue of its origin or manipulation: (i) is not associated with all of a nucleic acid with which it is associated in nature; (ii) is linked to a nucleic acid or other chemical moiety other than that to which it is linked in nature; or (iii) does not occur in nature.

One significant feature of the present cosmetic compositions is that the non naturally-occurring extracellular matrix proteins of the invention have not previously been cross-linked. By "not previously cross-linked" is meant that the proteins of the cosmetic compositions:

a. have not been cross-linked inside a body; or
b. are a non naturally-occurring soluble precursor (for example, recombinantly derived procollagen and tropoelastin) of an extracellular matrix protein that, when produced in a body, becomes cross-linked and insoluble (e.g., collagen, elastin). It will be noted that laminin or fibronectin do not ordinarily become crosslinked when expressed in a body.

The term "soluble" refers to solubility of the precursor in aqueous solutions, including water, physiological saline, blood, organic solvents, and lymph.

As used herein, the term "allelic variants" refers to different versions of a protein, or a gene encoding that protein, present in the human population. Protein variants can differ from one another by addition, substitution, or deletion of one or more amino acids. Typically, such proteins are produced from gene variants that differ from one another by addition, substitution, or deletion of one or more nucleotides[2]. Alternatively or additionally, such protein variants can be produced by alternative splicing or other processing of genetic sequences.

Extracellular Matrix Proteins and Polypeptides

As discussed above, the present invention provides cosmetic compositions formulated from non-naturally-occurring extracellular matrix proteins. These proteins may be derived from mammals such as cows, sheep or pigs. Preferably, however, the inventive compositions utilize human extracellular matrix proteins. Particularly preferred proteins used in the cosmetic compositions of the invention are human procollagen, human tropoelastin and human fibronectin.

Procollagen is generally considered to include the soluble precursors of the various forms of collagen. The chemical structure of the various procollagens suggests that the collagen molecule is relatively large and complex, each of the three constituent chains exhibiting an $M_r$ of between 140,000–180,000. Cloned cDNA's for human procollagen type I chains have been established. Chu et al., *Nucleic Acids Res.*, 10:5925, 1982; Myers et al., *Proc. Natl. Acad. Sci. USA*, 78:3516, 1981, each of which is incorporated herein by reference.

Tropoelastin is a soluble polypeptide having an amino acid composition very similar to that of insoluble elastin except for the absence of cross-links and a corresponding increase in lysine residues. The total lysine content is 38 residues per mole tropoelastin compared to about 6 residues per mole in native, cross-linked elastin. Tropoelastins from all species tested share a number of features in addition to their similarity in amino acid compositions, including a molecular weight between 72 kD to 74 kD, unusually high content of hydrophobic amino acids, high solubility in concentrated solutions of short chain alcohols, and a negative temperature coefficient of solubility in salt solutions. That is, solutions of tropoelastin undergo a phase separation upon raising the temperature from 4° C. to greater than 25° C. As a result, tropoelastin is notoriously difficult to extract from epithelial cells because of its unusual solubility properties and great susceptibility to proteolytic cleavage.

Human tropoelastin, in particular, contains about 750 amino acids. The primary amino acid sequence of human tropoelastin is encoded by a 3.5 kb mRNA and consists of alternating hydrophobic domains (rich in proline, glycine, and valine) and putative cross-linking regions (rich in alanine and lysine). See Fazio et al., *J. Invest. Dermatol.*, 91:458, 1988, incorporated herein by reference.

The extracellular matrix proteins utilized in the present invention may be prepared by any of a variety of available techniques, but it is important that the proteins do not go through a crosslinking step that must be reversed to solubilize the proteins as discussed above.

In some preferred embodiments of the invention, the proteins are synthesized using available chemical synthetic methods. For example, non-naturally occurring extracellular matrix proteins can be synthesized using an appropriate solid state synthetic procedure. Steward and Young, *Solid Phase Peptide Synthesis*, Freemantle, San Francisco, Calif. (1968). A preferred method is the Merrifield process. Merrifield, *Recent Prog. Hormone Res.*, 23:451, 1967.

Alternatively, the proteins can be prepared using recombinant procedures. Recombinant protocols for isolating non-naturally occurring extracellular matrix proteins from mammals, in particular from non-human mammals such as cows, pigs, monkeys and the like, generally involve isolating total messenger RNA from mammalian tissues or from cell lines likely to express a protein and then expressing the protein in an appropriate expression system.

Typically, total RNA from a tissue or cell culture is isolated using conventional methods. Subsequent isolation of mRNA is typically accomplished by oligo (dT) chromatography. Messenger RNA is size-fractionated by electrophoresis and the RNA transcripts are transferred to, for example, nitrocellulose according to conventional protocols (Sambrook, J. et al., *Molecular Cloning: A Laboratory*

*Manual,* Cold Spring Harbor Press, N.Y., 1989, incorporated herein by reference). For example, a labelled polymerase chain reaction (PCR)-generated probe capable of hybridizing with human elastin nucleotide sequences (see Fazio et al., supra) can serve to identify RNA transcripts complementary to at least a portion of the desired extracellular matrix protein gene. For example, if Northern analysis indicates that RNA isolated from a pig epithelium hybridizes with the labelled probe, then a pig epithelium cells are utilized for preparation of a cDNA library to be screened for the desired gene.

Northern analysis can be used to confirm the presence in the library of mRNA fragments which hybridize to a probe corresponding to all or part of the relevant gene. Northern analysis reveals the presence and size of the transcript. This allows one to determine whether a given cDNA clone is long enough to encompass the entire transcript or whether it is necessary to obtain further clones in order to generate a full-length cDNA, i.e., if the length of the cDNA clone is less than the length of RNA transcripts as seen by Northern analysis. If the cDNA is not long enough, it is necessary to perform several steps such as: (i) re-screen the same library with the longest probes available to identify a longer cDNA; (ii) screen a different cDNA library with the longest probe; and (iii) prepare a primer-extended cDNA library using a specific nucleotide primer corresponding to a region close to, but not at, the most 5' available region. This nucleotide sequence is used to prime reverse transcription. The primer extended library is then screened with the probe corresponding to available sequences located at 5' to the primer. See for example, Rupp et al., *Neuron,* 6:811, 1991.

The preferred clone utilized for expression has a complete coding sequence, i.e., one that begins with methionine, ends with a stop codon, and preferably has another in-frame stop codon 5' to the first methionine. It is also desirable to have a cDNA that includes all of the 5' and 3' untranslated sequences. To assemble a long clone from short fragments, the full-length sequence is determined by aligning the fragments based upon overlapping sequences. Thereafter, the full-length clone is prepared by ligating the fragments together using the appropriate restriction enzymes.

Of course, as will be appreciated by those of ordinary skill in the art, the above-described screening procedure is just one approach to isolation of genes to allow for recombinant expression of proteins. To name but one acceptable modification of the approach, an oligonucleotide probe may be employed instead of a PCR-generated probe to screen the library. An oligodeoxynucleotide probe typically has a sequence somewhat longer than that used for the PCR primers. A longer sequence is preferable for the probe, and it is important that codon degeneracy be minimized. A representative protocol for the preparation of an oligonucleotide probe for screening a cDNA library is described in Sambrook et al., *Molecular Cloning: A Laboratory Manual,* Cold Spring Harbor Press, New York, 1989. In general, the probe is labelled, e.g., $^{32}P$, and used to screen clones of a cDNA or genomic library.

As another modification, the library need not be screened by hybridization at all, but rather can be prepared as an expression library that can be screened using conventional immunization techniques, such as those described in Harlowe and Lane, D., *Antibodies,* Cold Spring Harbor Press, New York, 1988. Antibodies prepared using purified protein as an immunogen are preferably first tested for cross reactivity with the homolog of protein from other species.

In yet another version, a cDNA library is screened using the polymerase chain reaction (PCR). PCR screening permits the use of small samples for analysis. This technique depends upon the ability to amplify small amounts of epidermal mRNA or DNA using PCR and is based on procedures outlined in standard protocols. See, for example, Sambrook et al., supra. For example, a sample comprising as few as a thousand to as many as hundred thousand is extracted to release total RNA. The RNA is converted to cDNA by using reverse transcriptase. See Example 2. The cDNA created is amplified in the same reaction mixture using PCR. Primers for the PCR reaction are preferably designed to hybridize to opposite ends of the relevant messenger RNA sequence, thus amplifying the entire mRNA segment.

To obtain maximum specificity and yield in PCR, one must adjust a variety of reaction parameters, well known to those of ordinary skill in the art. The primers should have 40–60% G+C content, no long stretches of any one base, and no interprimer complementarity longer than two bases, especially at the 3' ends. Given these conditions, the following steps may increase the specificity of PCR: the reaction can be run with primer, template, and dNTP concentrations in the middle of the recommended range, using 2.5 units of Taq DNA polymerase, using an annealing temperature at least 10 degrees C. lower than optimal. If nonspecific products are observed, one may optimize the annealing temperature and adjust the primer and dNTP concentrations.

Recombinant methods for producing the particularly preferred, non-naturally occurring human extracellular matrix proteins of the invention are readily available. One method involves constructing a human cDNA library and screening it for extracellular matrix protein cDNAs. The resulting clones can be introduced into an expression vector system and proteins expressed and purified using standardized methods. See, for example, Sambrook et al., *Molecular Cloning: A Laboratory Manual,* Cold Spring Harbor Press, 1989. The recombinant proteins thus produced can be characterized by, for example, polyacrylamide gel electrophoresis (PAGE) analysis, and N-terminal sequencing.

In one particular preferred embodiment of the present invention, a human cDNA library either prepared from a selected individual as described below or purchased from a commercial source (e.g., Clontech, Palo Alto, Calif.) is screened to identify cDNAs encoding human tropoelastin. Positive clones are subject to sequencing and can be characterized by restriction endonuclease digestion followed by separation of DNA fragments. The smaller fragments are then used to isolate and re-screen the original cDNA library. Variations in sequence among identified cDNAs indicate the presence of isomorphic forms and/or allelic variants of the protein (see below).

For example, cDNAs encoding human tropoelastin can be isolated from a human epithelial cDNA library through PCR screening. Exemplary 25-mer PCR primer sequences and their position on the tropoelastin nucleotide sequence (as per Fazio et al., supra) are shown in Tables 1 and 2 for the 5' and 3' ends of tropoelastin, respectively. In Table 1 the base immediately upstream of the adenine in the start codon (ATG) is nucleotide number 1. Table 2 shows sequences complementary to the primary transcript of human tropoelastin at the 3' end. Similar primers may be generated by those of ordinary skill in the art from known mRNA sequences of other proteins. Once the appropriate clones have been isolated, the extracellular matrix proteins may be expressed and purified.

TABLE 1

HUMAN TROPOELASTIN PCR PRIMER DESIGN (5' END)

| SEQ ID NO.: | POSITION | GC % |
| --- | --- | --- |
| 1 | -10→-15 | 64 |
| 2 | -11→-14 | 60 |
| 3 | -12→-13 | 60 |
| 4 | -13→-12 | 60 |
| 5 | -14→-11 | 64 |
| 6 | -15→-10 | 64 |
| 7 | -16→-9 | 68 |
| 8 | -17→-8 | 68 |
| 9 | -18→-7 | 64 |
| 10 | -19→-6 | 64 |
| 11 | -20→-5 | 64 |
| 12 | -21→-4 | 64 |
| 13 | -22→-3 | 64 |
| 14 | -23→-2 | 68 |
| 15 | -25→-1 | 68 |
| 16 | -27→-3 | 68 |
| 17 | -28→-4 | 68 |
| 18 | -29→-5 | 68 |
| 19 | -30→-6 | 68 |
| 20 | -31→-7 | 68 |

TABLE 2

HUMAN TROPOELASTIN PCR PRIMER DESIGN (3' END)

| SEQ ID NO.: | POSITION | GC % |
| --- | --- | --- |
| 21 | -5→-20 | 64 |
| 22 | -6→-19 | 68 |
| 23 | -7→-18 | 68 |
| 24 | -8→-17 | 68 |
| 25 | -9→-16 | 68 |
| 26 | -10→-15 | 68 |
| 27 | -11→-14 | 68 |
| 28 | -12→-13 | 64 |
| 29 | -13→-12 | 64 |
| 30 | -14→-11 | 64 |
| 31 | -15→-10 | 60 |
| 32 | -16→-9 | 60 |
| 33 | -17→-8 | 60 |
| 34 | -18→-7 | 56 |
| 35 | -19→-6 | 52 |

However the desired genes are isolated, proteins can be expressed in any desirable expression system, including in vivo or in vitro systems. Well known in vivo expression systems utilize prokaryotic and/or eukaryotic (i.e., yeast, human) cells. See, for example, "Gene Expression Technology", Volume 185, *Methods in Enzymology*, (ed. D. V. Goeddel), Academic Press Inc., 1990, incorporated herein by reference.

A large number of vectors have been constructed that contain powerful promoters that generate large amounts of mRNA complementary to cloned sequences of DNA introduced into the vector. For example, and not by way of limitation, expression of eukaryotic nucleotide sequences in *E. coli* may be accomplished using lac, trp, lambda, and recA promoters. See, for example, "Expression in *Escherichia coli*", Section II, pp. 11–195, V. 185, *Methods in Enzymology*, supra; see also Hawley, D. K., and McClure, W. R., "Compilation and Analysis of *Escherichia coli* promoter DNA sequences", *Nucl. Acids Res.*, 11:4891, 1983, incorporated herein by reference. Expression of any desired extracellular matrix protein (including, for example, a human tropoelastin) in a recombinant bacterial expression system can be readily accomplished. See Example 4.

Yeast cells suitable for expression of the proteins of the invention include the many strains of *Saccharomyces cerevisiae* as well as *Pichia pastoris*. See, "Heterologous Gene Expression in Yeast", Section IV, pp. 231–482, V. 185, *Methods in Enzymology*, supra, incorporated herein by reference. Moreover, a large number of vector-mammalian host systems known in the art may be used. See, Sambrook et al., Volume III, supra and "Expression of Heterologous Genes in Mammalian Cells", Section V, pp. 485–596, V. 185, *Methods in Enzymology*, supra, incorporated herein by reference.

Suitable expression systems include those that transiently or stably expressed DNA and those that involve viral expression vectors derived from simian virus 40 (SV 40), retroviruses, and baculoviruses. These vectors usually supply a promoter and other elements such as enhancers, splice acceptor and/or donor sequences, and polyadenylation signals. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript® (Stratagene) plasmid derivatives. Recombinant molecules can be introduced into host cells via transformation, transfection, infection, electroporation, etc. Generally, introduction of protein molecules into a host is accomplished using a vector containing protein DNA under control by regulatory regions of the DNA that function in the host cell.

Certain preferred expression systems provide for overproduction of a recombinant extracellular matrix protein. See, for example, the overproduction methods described in U.S. Pat. No. 4,820,642 (Edman et al., Apr. 11, 1989), incorporated herein by reference. The general requirements for preparing one form of expression vector capable of overexpression are: (1) the presence of a gene (e.g., a prokaryotic gene) into which an extracellular matrix deoxyribonucleotide sequence can be inserted; (2) the promoter of this prokaryotic gene; and (3) a second promoter located upstream from the prokaryotic gene promoter which overrides the prokaryotic gene promoter, resulting in overproduction of the extracellular matrix protein. The second promoter is obtained in any suitable manner.

Alternate methods of expressing the proteins of the invention involve generation of transgenic animals, especially mammals such as cows and goats. A "transgenic animal" is an animal having cells that contain DNA which has been artificially inserted into a cell, which DNA becomes part of the genome of the animal which develops from that cell. The preferred DNA contains nucleotide sequences that encode soluble, extracellular matrix proteins and may be entirely foreign to the transgenic animal or may be homologous to the natural gene of the transgenic animal, but which is inserted into the animal's genome at a location which differs from that of the natural gene.

Once the recombinant proteins or polypeptides of the present invention are expressed, they may be isolated and purified by standard methods including chromatography (e.g., ion exchange, affinity, and sizing column chromatography), centrifugation, differential solubility, or by any other standard technique for the purification of proteins. See, for example, Scopes, "Protein Purification; principles and practice", 2nd edition, Springer-Verlag, New York, 1987, incorporated herein by reference.

For immunoaffinity chromatography in particular, an extracellular matrix protein of the invention encoded by human nucleotide sequences may be isolated by binding it to an affinity column comprising antibodies that were raised against that protein, and were affixed to a stationary support. Alternatively, affinity tags such as influenza coat sequence, and glutathione-S-transferase can be attached to the proteins of the invention to allow easy purification by passage over an appropriate affinity column.

Fragments

The cosmetic compositions of the present invention may utilize full-length proteins or alternatively may employ protein fragments. Fragments may be generated, for example, throgh expression of only partial coding sequences, or they may be generated directly from the intact protein.

Proteins are specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the ε-amino groups of lysine with ethyltrifluorothioacetate in mildly basic solution yields a blocked amino acid residue whose adjacent peptide bond is no longer susceptible to hydrolysis by trypsin. Goldberger et al. *Biochem.,* 1:401, 1962. Treatment of such a polypeptide with trypsin thus cleaves only at the arginyl residues.

One preferred modification (see below) of extracellular matrix proteins (or extracellular matrix protein genes) according to the present invention is therefore to render the proteins susceptible to proteolytic enzyme catalyzed hydrolysis. For example, alkylation of cysteine residues with δ-halo ethylamines yields peptide linkages that are hydrolyzed by trypsin. Lindley, *Nature,* 178:647, 1956. In addition, chemical reagents that cleave polypeptide chains at specific residues can be used. Withcop, *Adv. Protein Chem.* 16:221, 1961. For example, cyanogen bromide cleaves polypeptides at methionine residues. Gross et al., *J. Am Chem Soc.,* 83:1510, 1961. Thus, by treating the proteins of the invention with various combinations of modifiers, proteolytic enzymes and/or chemical reagents, numerous discrete overlapping peptides of varying sizes are generated. These peptide fragments can be isolated and purified from such digests by chromatographic methods.

Modifications

In certain preferred embodiments of the present invention, the non-naturally occurring extracellular matrix proteins utilized in the inventive cosmetic compositions include a moiety designed to improve or enhance the protein's function. For example, the proteins of the present invention can be linked to a moiety that: (i) enhances the skin penetration capabilities of the protein; (ii) enhances the water or oil solubility of the protein; and/or (iii) enhances the ability of the protein to act as a surfactant. These additional moieties may be present in the naturally occurring (i.e., native) protein. Nevertheless, if they are present in the native protein, the additional moieties: (i) are linked to the present, non-naturally occurring extracellular matrix proteins of the invention at a different position than they are in the native protein; and/or (ii) are present in the non-naturally occurring extracellular matrix proteins of the invention in amounts that differ from those that are in the native protein.

These additional moieties can include a variety of substances and chemical compounds, including, but not limited to liposomes, fatty acids, carbohydrates, lipids, proteins and the like. The most preferred moieties are peptide sequences. The additional sequences can be located at any position in the protein chain. Preferably, they are located at the amino-terminal end of the protein, the carboxy-terminal end of the protein, or both aminoand carboxy termini.

Additional moieties may be introduced into the proteins at the nucleotide level by expressing fusion proteins in the appropriate expression system such as in Example 3. Further aspects of the invention therefore pertain to cosmetics in which the non-naturally occurring extracellular matrix proteins are encoded by non-naturally occurring nucleotide sequences that may have additional nucleotide sequences combined with them. These additional nucleotide sequences preferably encode amino acid sequence moieties selected from the group consisting of hydrophilic amino acid sequences, hydrophobic amino acid sequences, lysine-rich amino acid sequences, and combinations of the foregoing sequences.

The additional nucleotide sequences may be linked so that the extracellular matrix protein of the invention, when expressed in a suitable expression system, contains the additional amino acid moieties either: (i) internally; (ii) at the amino-terminus, the carboxy-terminus, and/or both aminoand carboxy-termini of the protein.

In particular, preferred additional nucleotide sequences that introduce amino-terminal amino acids have the formula (I):

$$\text{ATG}—(\text{NNN})_x—; \quad\quad\quad (I)$$

where A=adenylic acid, T=thymidylic acid, and G=guanylic acid, all joined to each other by phosphodiester bonds;

where x=1 to 20;

where N=a nucleotide base, such as for example, adenine, thymine, cytosine, guanine, uracil;

where $(NNN)_x$=a plurality of codons.

The term "N", can also include modified bases such as, but not limited to, 4-acetylcytidine, 5-(carboxyhydroxymethyl) uridine, 2'-O-methylcytidine, dihydrouridine, the methylpseudouridines, inosine, 1-methyladenosine, 1-methylguanosine, N6-methyladenosine, and others.

Nucleotide sequences of this formula may be linked to the nucleotide sequence of an extracellular matrix protein of the invention so that the amino-terminal end of the encoded protein contains a hydrophobic amino acid sequence moiety having amino acids selected from the group consisting of, for example, phenylalanine (encoded by the triplets UUU and UUC), tryptophan (encoded by the triplet UGG), proline (encoded by the triplets CCU, CCC, CCA, and CCG), glycine (encoded by the triplets GGU, GGC, GGA, and GGG), valine (encoded by the triplets GUU, GUC, GUA, and GUG) and combinations of the foregoing amino acids. Likewise, additional nucleotide sequences encoding for amino acids that are to be linked at the amino-terminus can also encode hydrophilic amino acid sequence moieties having amino acids selected from the group consisting of, for example, aspartic acid (encoded by the triplets GAU and GAC), glutamic acid (encoded by the triplets GAA and GAG), and combinations of the foregoing amino acids. Further, nucleotide sequences can include lysine-rich amino acid sequence moieties (encoded by the triplets AAA and AAG). The term "lysine-rich" means amino acid sequences containing at least 30 percent lysine residues.

Alternative or additional added nucleotide sequences may encode amino acid moieties that can be linked at the carboxy-terminus of the extracellular matrix protein. In this case, the added nucleotides have the formula (II):

$$—(\text{NNN})_x—\text{TGA}; \quad\quad\quad (II)$$

where A=adenylic acid, T=thymidylic acid, and G=guanylic acid, all joined to each other by phosphodiester bonds;

where x=1 to 20;

where N=a nucleotide base, such as for example, adenine, thymine, cytosine, guanine, uracil;

where $(NNN)_x$=a plurality of codons.

The term "N", can also include modified bases such as, but not limited to, 4-acetylcytidine, 5-(carboxyhydroxymethyl)uridine, 2'-O-methylcytidine, dihydrouridine, the methylpseudouridines, inosine, 1-methyladenosine, 1-methylguanosine, N6-methyladenosine, and others.

The codons can encode a hydrophobic amino acid sequence moiety having amino acids selected from the group consisting of, for example, phenylalanine, tryptophan, proline, glycine, valine, and combinations of the foregoing amino acids. Likewise, hydrophilic and lysine-rich amino acid moieties can be added at the carboxy-terminus of the protein of the invention, using nucleotides encoding amino acid sequences as described above. Hydrophobic amino acid sequences tend to increase the lipid solubility of the protein of the invention. Hydrophilic amino acids serve to increase the water solubility of the protein. Lysine-rich amino acid sequences enhance the cross-linking of the extracellular matrix protein.

Positioning sequence moieties at both the amino and carboxy-termini of the proteins of the invention will enhance the amphipathic properties of the extracellular matrix protein. "Amphipathic" refers to a molecule that has both hydrophilic and hydrophobic groups. Amphipathic molecules are good emulsifiers (i.e., they can disperse one liquid into a second, immiscible liquid) and surfactants (i.e., they can reduce the surface tension of liquids or reduce interfacial tension between two liquids or a liquid and a solid).

Additional moieties may also be introduced into the proteins of the invention by conjugating the moieties to the expressed extracellular matrix protein using a variety of well-characterized linker molecules. Those of ordinary skill in the art will recognize that a large variety of possible linkers can be used with the proteins of the invention. See, for example, *Contributions to Microbiology and Immunology,* J. M. Cruse and R. E. Lewis, Jr (eds). Carger Press, New York, (1989), the entire contents of which are incorporated herein by reference. The conjugation of the proteins of the invention to another moiety (e.g. hydrophilic amino acid sequences) can be accomplished by any chemical reaction that will bind the two molecules so long as both molecules retain their respective activity. This linkage can include many chemical mechanisms, for instance covalent binding, affinity binding, intercalation, coordinate binding and complexation.

The preferred binding is, however, covalent binding. The covalent binding can be achieved either by direct condensation of existing side chains or by the incorporation of external bridging molecules. Many bivalent or polyvalent linking agents are useful in coupling protein molecules to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen et al., *J. Immunol.* 133:1335, 1984; Jansen et al., *Immuno. Rev.* 62:185, 1982; and Vitetta et al., supra).

Preferred linkers for coupling a moiety to the proteins of the invention are described in the literature. See, for example, Ramakrishnan et al., *Cancer Res.* 44:201, 1984 describing use of MBS (M-maleimidobenzoyl-N-hydroxysuccinimide ester). See also, Umemoto et al. U.S. Pat. No. 5,030,719, describing use of a halogenated acetyl hydrazide derivative coupled to an antibody by way of an oligopeptide linker. Particularly preferred linkers include: (i) EDC (1-ethyl-3-(3-dimethylamino-propyl)carbodiimide hydrochloride (see Example 4); (ii) SMPT (4-succinimidyloxycarbonyl-alpha-methyl-alpha-(2-pyridyl-dithio)-toluene (Pierce Chem. Co., Cat. #21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)propianamide] hexanoate (Pierce Chem. Co. Cat. #21650G); and (v) sulfo-NHS (N-hydroxysulfo-succinimide: Pierce Chem. Co., Cat. #24510) conjugated to EDC.

The linkers described above contain components that have different attributes, thus leading to molecules with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form molecules with increased stability. Disulfide linkages, are in general, less stable than other linkages because the disulfide linkage is cleaved in vivo, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodiimide coupling reaction alone.

Modification of the extracellular matrix proteins for use in the present invention can be achieved by exploiting in vivo processing activity of a host or by in vitro chemical means, e.g., by phosphorylation, glycosylation, crosslinking, acylation, proteolytic cleavage, linkage to an antibody molecule, membrane molecule or other ligand, (Ferguson et al., *Ann. Rev. Biochem.* 57:285, 1988.

In addition, the nucleic acid sequences encoding proteins of the invention may be engineered so as to modify processing or expression. For example, and not by way of limitation, nucleotide sequence(s) encoding the non-naturally occurring extracellular matrix proteins may be combined with a promoter sequence and/or a ribosome binding site using well characterized methods, and thereby facilitate harvesting or bioavailability.

Additionally, a given nucleotide sequence can be mutated in vitro or in vivo, to create variations in coding regions and/or form new restriction endonuclease sites or destroy preexisting ones, to facilitate further in vitro modification. Any technique for mutagenesis known in the art can be used including, but not limited to, in vitro site-directed mutagenesis (Hutchinson et al., *J. Biol. Chem.* 253:6551, 1978), use of TAB® linkers (Pharmacia), PCR-directed mutagenesis, and the like.

Of course, modified polypeptides or proteins for use in accordance with the present invention need not be produced via recombinant techniques. Synthetic methods for providing a variety of peptides based on collagen and tropoelastin have been described. These methods provide for synthesis of structural proteins having altered functional and chemical properties. See, U.S. Pat. Nos. 4,474,851 (Urry) and 4,898,926 (Urry), incorporated herein by reference.

Certain preferred modifications to the extracellular matrix proteins utilized in accordance with the present invention include changes that reduce the likely antigenicity of the proteins. As noted above, the mere fact that the present invention utilizes soluble proteins already reduces the likelihood that these proteins will induce an immune response; alternately or additionally, the amino acid sequence of the non-naturally occurring extracellular matrix protein(s) intended to be used in the cosmetic compositions may be analyzed in order to identify portions of the molecule that may be associated with decreased immunogenicity.

For example, the amino acid sequence may be subjected to computer analysis to identify surface epitopes which present computer-generated plots of antigenic index, an amphophilic helix, amphiphilic sheet, hydrophilicity, and the like.

Allelic Variants

As will be appreciated by those of ordinary skill in the art, multiple versions, or allelic variants, of the extracellular matrix proteins discussed herein are present in the population at large. Such allelic variants differ from one another in the substitution, addition, or deletion of one or more amino acids. Often, these protein sequence differences reflect differences in the genomic sequence of the genetic alleles encoding the proteins. In other cases, the same genomic sequence encodes more than one allelic variant protein because of differences in RNA splicing, RNA editing, other RNA processing, or translational or post-translational events.

One aspect of the present invention is the recognition that individuals within the population will express different collections of extracellular matrix protein allelic variants in their epidermis. Each individual might even have a unique constellation of such variants; the particular collection present in a given individual's epidermis can therefore be thought of as an "extracellular matrix fingerprint". In a preferred embodiment of the present invention, cosmetic compositions are formulated to re-create part or all of the extracellular matrix fingerprint of a selected individual (see below for further discussion).

Protein allelic variants produced by alternative splicing are herein referred to as protein "isoforms" or "isomorphs". It has been shown that elastin, fibronectin and collagen cDNA sequences reveal considerable variability in their primary nucleotide sequences, likely due to alternative splicing. See, for example, Fazio et al., *Lab. Invest.*, 58(3):270, 1988, incorporated herein by reference.

Briefly, most eukaryotic DNA protein coding genes contain sequences present in the corresponding mature mRNA in discontinuous genomic DNA segments (exons) interspersed among sequences (introns) that do not form a part of the mature mRNA. These intron sequences are precisely excised by a multistep process. The majority of instances studied so far, each and every one of the exons present in a gene are incorporated into one mature mRNA through the invariant ligation of consecutive pairs of donor and acceptor splice sites, removing every intron. This type of "constitutive" splicing yields a single gene product from each transcriptional unit even when its coding sequence is split into many exons.

There are instances, however, in which nonconsecutive exons are joined in the processing of some, but not all, transcripts from a single gene. This "alternative" pattern of splicing can exclude individual exon sequences from the mature mRNA in some transcripts but include them in others. The use of such alternative splicing patterns in transcripts from a single gene yields mRNA's with different primary structures. When the exons involved contain translated sequences, these alternatively spliced mRNA's will encode related but distinct proteins, hereinafter referred to as "isomorphs". The capacity to generate different, but closely related protein isomorphs by alternative splicing increases significantly the phenotypic variability that can be obtained from single genes such as fibronectin, collagen, or elastin.

The consequences of alternate splicing of protein mRNA are significant. For example, in the case of fibronectin, alternative splicing has been shown to lead to synthesis of isomorphs of the protein with different physical, chemical, and functional properties. Kornblitth et al., *EMBO J.*, 4:1755, 1985.

Table 3 below summarizes the available information on isomorphic forms of human tropoelastin.

TABLE 3

ISOMORPHS OF HUMAN TROPOELASTIN

| Human elastin sequence | Deleted Exons | Reference | Exon Location[a] |
|---|---|---|---|
| cHDE 1 | 4 | (1) | |
| cHDE 2 | 4 | (1) | |
| cHDE 3* | 12A | (1) | 1415–1432 |
| | 13 | | 1358–1414 |
| cHDE 4* | 4 | (1) | 2051–2104 |
| | 4A | | 2105–2149 |
| | 12A | | 1415–1432 |
| cHDE 5* | 12A | (1) | 1415–1432 |
| cHDE 6 | 4, 12A | (1) | |
| cHDE 7 | 4, 12A | (1) | |
| CHEL 2 | none | (2) | |
| CHEL 3* | 10 | (2) | 1640–1765 |
| CHEL 4* | 4 | (2) | 2051–2104 |
| | 10 | | 1640–1765 |
| | 13 | | 1358–1414 |
| cHE 1 | 4 | (3) | |
| cHE 2* | 4 | (3) | 2051–2104 |
| | 4A | | 2105–2149 |
| cHE 3 | none | (3) | |
| cHE 4* | 4 | (3) | 2051–2104 |
| | 13 | | 1358–1414 |

[a]Base pair numbering of deleted exons according to Fazio et al., (reference 1)
*Unique isomorph sequence combinations
(1)-Fazio et al., J. Invest. Derm., 91:458, 1988
(2)-Indik et al., Proc. Nat. Acad. Sci. USA, 84:5680, 1987
(3)-Fazio et al., Lab. Invest., 58:270, 1988

Preparation of isomorphic forms of extracellular matrix proteins is relatively straightforward, once the protein message has been isolated. For example, once the known tropoelastin messenger RNA has been amplified by the PCR method, one or more forms of the tropoelastin messenger RNA sequence are present in sufficient quantity for analysis. The presence or absence of any particular exon in the amplified sequence can be determined by cloning the amplified cDNA and determining the actual nucleotide sequence of the cloned gene.

Alternately or additionally, the presence or absence of any particular exon in the amplified sequence can be determined by preparing a series of probes of DNA based on known exon sequences (see Table 3 and references cited therein). The amplified DNA can be probed by hybridization for the presence or absence of each exon without directly sequencing the DNA. This method is generally preferable to the method described immediately above in that it is less time consuming and expensive. The DNA hybridization probes identify any missing exons and describe the sequence of the messenger RNA accurately enough so that it can be constructed in an expression system for eventual expression of that precise tropoelastin isomorph.

It is conceivable that the different isomorphs of tropoelastin that exist (based upon differences in the coding regions of tropoelastin messenger RNA) will also have altered biological properties. We note that tropoelastin exon 13 contains lysyl residues, potentially involved in cross-linking. Thus, covalent intermolecular cross-links between tropoelastin polypeptide may be affected by the deletion or insertion of exon 13 in different isomorphs. Of the 14 total known human tropoelastin sequences (cHDE, cHEL and cHE): three are missing exon 4; two are missing no exons; and two are missing exons 4 and 12A. The remaining 7 of 14 sequences (marked with the asterisk in Table 3) are unique isomophs.

Preparation of non-isomorphic allelic variants is equally straightforward in light of the teachings herein. When differences in protein sequence reflect differences in genomic DNA, pre-mRNA, mRNA, and/or edited or processed nucleic acids, the variants can be prepared as described above, through production of a cDNA library from the cells in which the variants are naturally produced.

When differences in protein sequence do not reflect nucleic acid sequence differences, they can nonetheless be identified by isolation of protein from cells in which the variant proteins are produced. The isolated proteins can then be subjected to any of a variety of analytical methods, including but not limited to immunological assays such as Western Blots or other binding studies, fragmentation studies, protein sequencing, etc. as is known in the art so that the precise chemical structure of the variants is determined. Once the chemical structure is known, cDNAs encoding that structure can be prepared (e.g., synthetically, through PCR, or using recombinant DNA technology) to allow easy preparation of large amounts of each individual variant.

It will be appreciated that analysis of proteins present in epidermis of an individual will necessarily involve analysis of the processed, crosslinked, insoluble forms of those proteins. The information gleaned from such analysis, however, allows preparation of analogous soluble proteins as described herein.

In certain preferred embodiments of the invention, cosmetic compositions are formulated to contain more than one allelic variant of the same protein; other preferred embodiments contain two or more different proteins, each of which may be present in more than one allelic forms. In especially preferred embodiments, the particular proteins and allelic variants are selected, and the composition is formulated, to reproduce the relative amounts of the proteins and/or allelic variants present in the skin of a selected (see below) individual.

Preferably, an individual whose skin characteristics are intended to be emulated is selected, the relative amounts of one or more extracellular matrix proteins or allelic variants are determined as described herein, each extracellular matrix protein or allelic variant is then produced separartely, preferably either synthetically or by expression of an engineered gene in a host cell, and the separately-produced proteins and/or variants are recombined together in ratios approximating those at which they are observed in the skin of the selected individual. Most preferably, the individual is a human.

Functional Equivalents

Cosmetic compositions of the present invention containing non-naturally occurring extracellular matrix proteins include, but are not limited to, those containing the primary amino acid sequence of elastin, collagen, their soluble precursors, isomorphs thereof, and the like. The non-naturally occurring extracellular matrix proteins may include altered sequences in which functionally equivalent amino acid residues are substituted for residues within the sequence, resulting in a silent change.

As alluded to previously with regard to the additional amino acid sequence moieties of the invention, a striking feature of the genetic code is its degeneracy; 61 codons (i.e., triplets) represent 20 amino acids. Almost every amino acid except tryptophan and methionine is represented by several codons. Often the base in the third position of a codon is not significant, because those amino acids having 4 different codons differ only in the third base. This feature, together with a tendency for similar amino acids to be represented by related codons, increases the probability that a single, random base change will result in no amino acid substitution or in one involving an amino acid of similar character. For example, a change of CUC to CUG has no effect since both codons represent leucine; a change of CUU to AUU results in replacement of leucine with isoleucine, a closely related amino acid.

According to the present invention, an amino acid is "functionally equivalent" compared with the known sequences of proteins if the amino acid sequence contains one or more amino acid residues within the sequence which can be substituted by another amino acid of a similar properties which acts in a functionally equivalent way to the original amino acid. Substitutes for an amino acid within the sequence may be selected from other members of the class to which the amino acid belongs. The non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid.

Substitutions are chosen for their effect on: (i) maintaining the structure of the peptide backbone in the area of the substitution, for example, as a sheet or helical conformation; (ii) maintaining the charge or hydrophobicity of the molecule; or (iii) maintaining the bulk of the side chain. The substitutions that in general are expected to induce greater changes, and that should be avoided, are those in which: (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

Most deletions and insertions in the proteins, however, are not expected to produce radical changes in the characteristics of the protein. Nevertheless, when it is difficult to predict the exact effect of the substitution, deletion, or insertion in advance of doing so, one skilled in the art will appreciate that the effect will be evaluated using routine screening assays as described below. For example, a change in the immunological character of a given protein, such as binding to a given antibody, is measured by an immunoassay such as a competitive type immunoassay. A change in solubility may be assayed, for example, by skin penetration tests.

Selection Criteria

Several of the selection criteria desirably used to formulate the cosmetic composition of the present invention have already been discussed, and will vary based upon the intended use of the cosmetic.

For example, it is generally desirable that the inventive cosmetic compositions not induce negative immune responses generally. As has been discussed, use of soluble extracellular matrix proteins avoids many of the problems encountered in the art in this regard. Additionally, various modifications can be made to minimize antigenicity problems, as is discussed above. In a particular instance in which a potential wearer of a cosmetic is interested in minimizing his or her immune reaction to that cosmetic, the invention provides a method for formulating a non-immugenic cosmetic: utilizing only extracellular matrix proteins that are found in epidermis of that individual, preferably in ratios approximating those at which they are found in the individual's skin.

Thus, in certain preferred embodiments of the invention, one or more extracellular matrix proteins or allelic variants is identified in the epidermis of a potential cosmetic wearer. The identified proteins or allelic variants are then individually prepared in soluble form, as described herein, and are combined together in ratios approximating those at which they are present in the skin of the potential wearer.

Furthermore, by using no more than routine methods, a series of cosmetic compositions can be prepared, each composition containing a different isomorphic form of a protein. In this way, cosmetics can be screened for skin responses using standard techniques. Those isomorphs that fail to generate a reaction can be used to prepare non-allergenic cosmetic compositions.

Reduced antigenicity is not the only selection criterion useful in accordance with the present invention. In particular, as has already been discussed, the present invention provides methods of formulating cosmetic compositions that mimic the extracellular matric protein composition of an individual having certain skin characteristics. For example, it is well known in the cosmetics industry that wearers of cosmetics desire to have youthful-appearing skin. In one particularly preferred embodiment of the present invention, an skin of human subjects is visually screened to select those subjects having the most youthful-appearing skin. One or more, prefereably at least two, extracellular matrix protein allelic variants are then identified as being produced by the subject's cells, and a cosmetic composition containing soluble forms of these allelic variants is prepared as described herein.

Those of ordinary skill in the art will recognize that there is no universally accepted standard of what constitutes "youthful-appearing skin". Generally, when a reasonable person would consider a subject's skin to have aspects (e.g., elasticity, tone, color) that typically characterize skin of a younger person, the subject is considered to have youthful-appearing skin. However, the present invention provides for the preferences of individual cosmetic wearer's or manufacturer's to be taken into account. As a "designer cosmetic" can be formulated as described herein to reproduce one or more aspects of the extracellular matrix protein composition of any individual, the wearer or formulator may select any person, on any basis, whose extracellular matrix composition is to be imitated. Preferred cosmetic compositions of the present invention can therefore be considered "recombinant cosmetics" and provide cosmetic preparations tailored to the individual subject.

Formulations

Once the extracellular matrix protein(s) to be utilized in the inventive cosmetic compositions have been prepared, the composition is fabricated into a cosmetic composition by combining the protein(s) with a cosmetic carrier. Any available cosmetic carrier may be utilized.

For example, the cosmetic carrier may take the form of fatty or nonfatty creams, milky suspensions or emulsion-in-oil or oil-in-water types, lotions, gels or jellies, colloidal or noncolloidal aqueous or oily solutions, pastes, aerosols, soluble tablets or sticks. The amount of preferred soluble extracellular matrix protein(s) combined with the cosmetic carriers according to the invention may vary between wide limits, depending upon the formulation, and the frequency of use of the composition. Generally, the carrier contains from about 0.001% to about 10% by weight of the proteins. Preferred ranges are about 0.1% to about 10%.

Extracellular matrix proteins according to the invention may also combined with surface active agents of the anionic, cationic or nonionic type, emulsifying agents, perfumes, solvents, fats, oils and mineral wax, fatty acids and derivatives thereof alcohols and derivatives thereof, glycols and derivatives thereof, glycerol and derivatives thereof, lanolin, beeswax, oleic acid, spermaceti, almond oil, castor oil, sorbitol and derivatives thereof, tracancanth gum, clay, magnesia, talc, metal stearates, chalk, magnesium carbonate, and the like. These materials are well-known in the cosmetic art and are discussed, for example, in Remington's *Pharmaceutical Science,* McCutcheon's *Detergents,* and Sagarin's *Science and Technology of Cosmetics,* all of which are incorporated herein by reference. Exemplary cosmetic compositions used according to the present invention are given in Example 1.

The cosmetic compositions used in the method according to the invention may also contain agents such as antibiotics, anti-inflammatories or anesthetics. More specifically, the soluble extracellular matrix proteins of the present invention may be combined with the following compounds, typically in a drop or ointment form with the preferred indicated typical dosages: carbenicillin (4 mg/ml); (50 mg/ml); chloramphenicol (5 mg/ml); gentamicin (8–15 mg/ml); penicillin G; polymyxin B; streptomycin; sulfacetamide; trifluridine; acyclovir; sulfadiazine; corticosteroids; nystatin; miconazole (3 mg/ml). The following anti-inflamatories may also be used in the invention; cortisone; prednisolone; dexamethasone.

The cosmetic compositions of the present invention may all contain various preservatives such as, butylated hydroxytoluene, methionine, cysteine, ascorbic acid, catalase, superoxide dismutase, glutathione, and the like. These examples are only illustrative and are not considered to limit the scope of the invention.

Assays

Any of a variety of assays can desirably be performed on the cosmetic compositions of the present invention, or components thereof, to ensure that they meet relevant formulation criteria.

For example, extracellular matrix proteins utilized in the inventive compositions are preferably highly purified. The purity of the proteins contained with the cosmetics of the invention may be tested by purifying the proteins using conventional methods, such as SDS gel electrophoresis and arbitrarily setting a purity standard (e.g., 95% purity) that meets or exceeds that purity need to pass the conventional skin testing assays described herein.

The extent to which the soluble extracellular matrix proteins penetrate into skin when applied in the inventive cosmetics can be assayed using any of a variety of known tests. For example, dermatologists have used strips of plastic adhesive tape to remove successive skin layers with each piece of tape. This removal may be verified by staining cells removed by each layer followed by histological examination. For most individuals, the outermost layer of the skin, consisting of dead cells, comprises about 12–18 layers of cells. After this number of layers has been stripped from the same site there appears what is known as a "glistening layer" of the epidermis, so-called because at this layer of tissue, fluid starts to ooze out of the living cells.

Penetration of the first layers of human skin with soluble extracellular matrix proteins of the present invention is determined by radioactively labeling the soluble proteins, preferably with tritium. For example, penetration by tropoelastin may be determined by reacting several ml of soluble protein with an equal volume of triatiated acetic anhydride at room temperature for several days to acylate one or more N-groups on the elastin molecule. The triatiated product is subject to repeated dialysis until a specific radioactivity (at least 500 counts per mg) is obtained. The resulting tritiated product is supplied to the forearm of a human subject. After remaining in place for several hours, tape stripings are taken from successive layers and placed in liquid scintillation counting vials for analysis. The number of counts is then determined as a function of the layers; thus the depth of penetration of the soluble protein can be determined.

A second method for assaying skin penetration involves radioactively labeling the protein by producing it recombinantly in a expression system containing radioactive amino acids, such as for example carbon-14 labeled valine. The valine, incorporated into the expressed protein, will be labeled and the expressed protein can be tested in the tape-stripping method illustrated above.

In yet another penetration assay method, marked areas of the back of the hand of human volunteers can be treated with the cosmetic composition of the present invention. Punch biopsies of the treated skin are taken and frozen sections are prepared. Using an antibody against the protein, (e.g., tropoelastin; see Indik et al., *Arch. Biochim. Biophys.*, 280:80, 1990) immunofluorescence tests are carried out in order to visualize the location of the protein.

The ability of the inventive cosmetic compositions to protect agains uv radiation can also be assayed using known procedures. For example, one series of tests is carried out with rats in which a part of the skin of the back of the rat is depilated and then exposed to ultraviolet radiation. A cream composition, for example as described in Example 1, is applied to the exposed skin of the treated rats and to the unexposed skin of control rats. The skin of the animals treated is observed for scaling.

The extent to which application of inventive cosmetic compositions alters skin elasticity can also be monitored, for example using the skin of old rats in which changes in the elastin and collagen networks and in the amount of mucopolysaccharide levels correlate well with similar changes in the skin of aged humans. See U.S. Pat. No. 4,007,266, incorporated herein by reference. In particular, male Wistar rats (about 30 months old and 400–500 g) have a skin strip of about 3 cm long by 0.5 cm wide removed from their backs parallel to the spinal cord. The strip is held stationary from the end closest to the head and a force of about 50 g applied for about 5 minutes. The length of the skin strip is measured after this traction period. This test permits a determination of the skin elasticity. Histological tests are also carried out to observe the thickness of the epidermis, the presence of ribonucleic acid in the basal cells of the epidermis, the structure of the different fibrillary elements of the dermis, such as collagen and elastin fibers, and the presence of mucopolysaccharides in the dermis. Skin specimens are preserved with Carnoy fixative or with neutral, buffererd formalin solution. Skin specimens are embedded in paraffin prior to slicing by a conventional microtome. For example, presence of ribonucleic acid content is measured by toluen blue staining at a pH of 3; dermal elastin is stained by the method of Wiegert with fuschine-resorcinol and by the method of Gomori with aldehyde-fushine.

EXAMPLES

The present invention will now be illustrated by the following non-limiting examples in which all percentages are weight percentages.

Example 1

Preparation of Cosmetic Compositions

Creams

A preferred cream (oil-in-water) containing the active composition includes the following materials:

a) glycerol monostearate: 12.0%;
   cetyl stearyl alcohol ethylene oxide adduct containing about 12 mole ethylene oxide: 1.5%;
   cetyl stearyl alcohol ethylene oxide adduct containing about 20 mole ethylene oxide: 1.5%;
   cetyl alcohol: 2.0%;
   2-octyl-dodecanol: 10.0%;
   isoctyl stearate: 8.0%;
   caprylic/capric acid triglyceride: 3.0%;
   methylparaben: 0.17%;
   propylparaben: 0.03%;

and b) distilled water: 46.8%
   glycerol: 5.0% and c) extracellular matrix protein according to the present invention (prepared as explained above): 10.0%

Mixture a) is heated to approximately 70° C. and mixture b) is likewise heated to approximately 70° C. and then added while stirring to mixture a).

Stirring is continued until the cream has cooled down to approximately 30° C. Then composition c) is added while stirring and the cream is homogenized.

By the term "cream" used herein are meant all cosmetic materials which include, for instance hand creams, cleansing creams, milky lotions, cold creams, vanishing creams, hair creams, foundation creams, beauty washes, and facial packs.

Emulsions

Preferred oil-in water emulsion (o/w) containing the soluble protein prepared according to the present invention includes the following materials:

a) glycerol monostearate: 3.0%;
   cetyl stearyl alcohol: 2.0%;
   cetyl stearyl alcohol ethylene oxide adduct containing about 12 mole ethylene oxide: 1.5%;
   cetyl stearyl alcohol ethylene oxide adduct containing about 20 mole ethylene oxide: 1.5%;
   glycerol monooleate: 0.5%;
   2-octyl-dodecanol: 10.0%;
   methylparaben: 0.17%;
   propylparaben: 0.03%; and b) distilled water: 66.3%;
   glycerol: 5.0%; and c) extracellular matrix protein according to the present invention (as in example 1): 10.0%

Mixture a) is heated to approximately 70° C. and mixture b) is likewise heated to approximately 70° C. and added while stirring to mixture a).

Stirring is continued until the o/w emulsion has cooled down to approximately 30° C. Then composition c) is added while stirring and the o/w emulsion is homogenized.

Gels

A gel containing a soluble protein according to the present invention includes the following materials:

a) distilled water: 65.1%;

polyacrylic acid (type Carbopol 940): 0.8%;

methylparaben: 0.17%;

propylparaben: 0.03%; and b) polyoxethylene (20) sorbitan trioleate: 0.3%;

sorbitan monooleate: 0.15%;

caprylic/capric acid triglyceride: 2.5% and;

c) distilled water: 20.1%;

triethanolamine: 0.8% and;

d) extracellular matrix protein according to the present invention (as in Example 1):

10.0%

Preparation of the gel is carried out as follows:

For obtaining a), polyacrylic acid is dispersed under rapid stirring in water; then the components of b) are mixed and added under stirring to a);

likewise the aqueous triethanolamine solution c) is added under stirring;

finally, composition d) is added under stirring.

Example 2

PCR Amplification of Tropoelastin cDNA

Oligonucleotides Used for Amplification

Oligonucleotides are synthesized on a Biosearch DNA synthesizer. Most of the primers are mRNA-specific primers. The 5' primers and 3' primers are designed to hybridize to opposite extremes of the particular elastin mRNA sequence.

Amplification Method

RNA is reverse transcribed into cDNA using conventional methods. Briefly, a 10-$\mu$l reverse transcription reaction mixture containing 1 $\mu$g of total cellular RNA, 1× PCR buffer (20 mM Tris HCl, pH 8.3, 50 mM KCl; 2.5 mM $MgCl_2$/100 $\mu$g of bovine serum albumin per ml), 1 mM dithiothreitol, 0.5 mM dNTP, 10 units of RNasin (Promega Biotec), 0.1 $\mu$g of oligo (dT) and 100 units of BRL Moloney murine leukemia virus reverse transcriptase (Bethesda Research Laboratories) is incubated at 37° C. for 60 min, heated to 95° C. for 5–10 min, and then quick-chilled on ice. PCR is performed at a final concentration of 1× PCR buffer/50 $\mu$M dNTPs/0.1 $\mu$M each 5' and 3' primers/1×$10^6$ cpm of $^{32}$P-end-labeled primer/1 unit of *Thermus aquaticus* DNA polymerase (Taq polymerase)(Perkin-Elmer/Cetus) in a total volume of 50 $\mu$l. The mixture is overlaid with mineral oil and then amplified with the Perkin-Elmer Cetus thermal cycler. The amplification profile involves denaturation at 95° C. for 30 sec, primer annealing at 55° C. for 30 sec. and extension at 72° C. for 1 min.

Example 3

Construction and Screening of a Human Skin Fibroblast cDNA Library

This method is adapted from Fazio et al., *J. Invest. Dermatol.*, 91:458, 1988, incorporated herein by reference.

Total RNA is isolated from cultured human skin fibroblasts (JIMM-69; established from a full-term fetus) using guanidinium isothiocyanate extraction followed by CsCl density gradient centrifugation, and used for synthesis of the cDNA library. The purified RNA is primed with oligo-dT, and first strand synthesis is catalyzed by cloned Maloney murine leukemia virus reverse transcriptase (BRL). The resultant RNA/DNA hybrid is subjected to RNase H digestion followed by second strand synthesis catalyzed by DNA polymerase I (See, Gubler et al., *Gene* 25:263, 1983. The cDNAs are blunt-ended, using T4 polymerase, and ligated into the phage vector gZAP (Stratagene, San Diego, Calif.) using EcoRI linkers. The cDNAs are packaged using GIGA Pack Extract (Stratagene). The bacteriophage library is plated using an *E. coli* strain XL-1-Blue (Stratagene).

Initial screening of approximately $10^6$ independent clones of the unamplified cDNA library is carried out in duplicate with two separate probes: a) cHE2, a 2.5 kb human placental elastin cDNA containing 1.5 kb of translated sequence (Fazio et al., *Lab. Invest.*, 58:270, 1988); and b) a 5', 400 bp subclone of cHE2 isolated by EcoRI-BamHI double restriction endonuclease digestion. These probes are radiolabeled by nick transaction with $\alpha[^{32}P]dCTP$ and used to screen the library by plaque hybridization.

Clones positive to both the 2.5 kb cDNA and its 5' subclone, are subjected to plaque purification, and the isolated recombinants digested with EcoRI endonuclease. Electrophoresis on 1% agarose gel, with comparison to standard DNA markers (New England Bio Labs, Beverly, Mass.), is used to estimate the size of the inserts.

Characterization of Elastin cDNA's

The newly isolated cDNAs are characterized by restriction endonuclease digestions, followed by separation of the DNA fragments on agarose gel electrophoresis. The appropriate DNA fragments are cloned into the phage vector M13 (mp18 and mp19; Boehringer Mannheim, Indianapolis, Ind.), and nucleotide sequencing performed using the dideoxy chain termination method (Sanger et al., *Proc. Natl. Acad. Sci. USA* 72:5463, 1977). Sequencing primers include the universal M13 17-mer primer, as well as appropriate oligonucleotides synthesized for extension of the sequencing.

Hybridization with Exon-specific Probes

Oligonucleotide sequences specific for individual exons are selected by computer-assisted analysis of the human elastin gene structure (Indik et al., *Proc. Natl. Acad. Sci. USA*, 84:5680, 1987; Indik et al., *Connect. Tissue Res.*, 16:197, 1987). The exon-specific oligonucleotides are synthesized using a modification of the phosphite method of Mateeucci (*J. Am. Chem. Soc.*, 103:3185, 1981) employing a MilliGen (Bedford, Mass.) programmable synthesizer. The synthetic oligonucleotides are purified by reverse phase high-pressure liquid chromatograph (Varian 5000).

Exon-specific synthetic oligonucleotides are radioactively labeled at the 5'-end, with $\gamma[^{32}P]dATP$, by a phosphate exchange reaction catalyzed by T4 polynucleotide kinase. For elucidation of the presence or absence of a specific exon sequence within the dermal fibroblast clones, 100 ng of the insert cDNA is denatured, dotted onto nitrocellulose filters, and hybridized with 10 ng of the radiolabeled exon-specific oligonucleotide probe. Filter prehybridization is performed in a solution consisting of 0.9 M NaCl, 90 mM sodium citrate (pH 7.0), 0.5% sodium dodecylsulfate, 100 ug/ml denatured salmon sperm DNA, 0.1% polyvinyl pyrrolidine, 0.1% bovine serum albumin, and 0.1% Ficoll, at 42° C. for 2 h. The hybridization, following addition of the labeled synthetic oligonucleotide probe, is carried out for 16 h in the same solution. The filters are washed at a final stringency of 0.15M NaCl, 15 mM sodium citrate, at 55° C. for 60 min.

Example 4

Production of Recombinant Human Tropoelastin

The following procedures are adopted from those of Indik et al., *Arch. Biochem. Biophys.*, 280:80, 1990, incorporated herein by reference.

Construction of Expression Vector

Tropoelastin cDNA, reverse transcribed from the mRNA of human epidermal cells (See Example 3) is cloned into a plasmid, such as pUC8. Preferably, the 2.2 kb EcoRI/HindIII fragment of the full length tropoelastin cDNA clone, cHEL2 (Indik et al., *Proc. Natl. Acad. Sci. USA* 84:5680, 1987), is subcloned into pUC8. The fragment includes an untranslated 5' region. Digestion of pUC8 with EcoRI and SstII removes a 48-base pair fragment containing the 5' noncoding sequence. This EcoRI/SstII fragment is then ligated to Oligomer 1 (see Indik et al., *Arch. Biochem. Biophys.*, supra). The completed sequence includes a 5' EcoRI site, a unique NcoI site, the tropoelastin sequence, and a 3' SstII site.

The 3' region is constructed by ligating Oligomer 2 ( Indik, *Arch. Biochem. Biophys.*, supra) to the HindIII site of the tropoelastin insert. Oligomer 2 contains a unique 3' HindIII site 21 base pairs upstream from the termination sequence (TGA). Oligomer 2 also contains the remainder of the tropoelastin sequence, an XbaI site, and a 3' EcoRI site. The repaired tropoelastin is cloned in the EcoRI site of pUC19, previously treated to remove HindIII, XbaI and BamHI sites. The resulting plasmid (pUC19-tropoelastin) is cleaved at the unique NcoI site at the 5' end of the tropoelastin sequence. The cleaved tropoelastin sequence is ligated to a synthetic oligonucleotide with a start codon having formula (I):

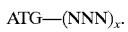

ATG—(NNN)$_x$.

Alternately, or in addition, the 3' terminus of the tropoelastin sequence can be cleaved at the HindIII site and ligated to a synthetic oligonucleotide with a stop codon having the formula (II):

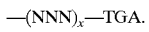

—(NNN)$_x$—TGA.

This insert can then be cloned into an expression vector containing the signal peptide, phage promoter region, and ribosome binding domain.

The plasmid pAS-MCS72, designed to express fusion proteins, (Indik et al., *Arch. Biochem. Biophys.*, supra) is an exemplary construction. This expression plasmid is created by ligating the ECORV/PvuII fragment of pOTSNC012 (Suskilkiemar et al., *Cell;* 36:43, 1984) which contains multiple cloning sites, into PASI EH801 (Young et al., *Proc. Natl. Acad. Sci. USA*, 80:6105, 1983) previously digested with NruI and PvuII. Thus, contained in pAS-MCS72 are a coding sequence for the influenza NS1 gene product, the P$_L$ promoter from phage lambda, the ribosome binding domain from lambda CII protein and the N antitermination function. An NcoI site within the NS1 gene provides in-frame cloning at the 5' end of the insert sequence. This construct allows for any insert protein lacking internal methionine residues (such as tropoelastin) to be separated from NS1 by CNBr cleavage.

The tropoelastin cDNA, containing the synthetic oligonucleotides in reading frame, cloned into, for example, pAS-MCS72, is transformed into the lysogenic host *E. coli* AR120, and transformants are selected using routine procedures. Bacteria bearing the expression plasmid induced by, for example, 60 mg/ml nalidixic acid, are shaken at 37° C. to allow for expression of the tropoelastin isomorph. Bacterial pellets are suspended in buffer, treated with lysozyme and then centrifuged. The pellet from the lysozyme treatment is suspended in buffer, homogenized, and centrifuged. The pellets, containing tropoelastin associated with the cell membranes, is treated with CNBr, releasing solubilized, intact tropoelastin fusion protein. Additional purification is achieved using reverse phase chromatography, or other method.

Example 5

Preparation of Constructions for Transfections and Microinjections

Methods for purification of DNA for microinjection are well known to those of ordinary skill in the art. See, for example, Hogan et al., *Manipulating the Mouse Embryo*, Cold spring Harbor Laboratory, Cold Spring Harbor, N.Y. (1986); and Palmer et al., *Nature*, 300:611, 1982.

Construction of Transgenic Animals

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA*, 82:4438, 1985). Embryos can also be infected with viruses, especially retroviruses, modified to bear nucleic acids encoding extracellular matrix proteins.

Pluripotent stem cells derived from the inner cell mass of the embryo and stabilized in culture can be manipulated in culture to incorporate nucleic acid sequences encoding proteins of the invention. A transgenic animal can be produced from such cells through implantation into a blastocyst that is implanted into a foster mother and allowed to come to term.

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. B6D2F$_1$ males can be used for mating and vasectomized Swiss Webster studs can be used to stimulate pseudopregnancy. Vasectomized mice and rats can be obtained from the supplier.

Microinjection Procedures

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia*, 47:897, 1991. Other procedures for introduction of DNA into tissues of animals are described in U.S. Pat. No. , 4,945,050 (Sanford et al., Jul. 30, 1990).

Transgenic Mice

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by CO$_2$ asphyxiation or cervical dislocation and embryos are recovered from excised oviducts and placed in Dulbecco's phosphate buffered saline (DPSS) with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The pipet tip is inserted into the infundibulum and the embryos transferred. After the transfer, the incision is closed by two sutures.

Transgenic Rats

The procedure for generating transgenic rats is similar to that of mice. See Hammer et al., *Cell*, 63:1099, 1990. Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPSS with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10–12 embryos are transferred into each rat oviduct through the infundibulum. The incision is then closed with sutures, and the foster mothers are housed singly.

Embryonic Stem (ES) Cell Methods

INTRODUCTION OF DNA INTO ES CELLS: Methods for the culturing of ES cells and the subsequent production of transgenic animals by the introduction of DNA into ES cells using methods such as electroporation, calcium phosphate/DNA precipitation; and direct injection are well known to those of ordinary skill in the art. See, for example, *Teratocarcinomas and Embryonic Stem Cells, A Practical Approach*, E. J. Robertson, ed., IRL Press (1987). Selection of the desired clone containing ES cells is accomplished through one of several means. Although embryonic stem cells are currently available for mice, it is expected that similar methods and procedures as described and cited here will be effective for embryonic stem cells from different species as they become available.

In cases involving random gene integration, a clone containing nucleic acid sequences encoding the soluble extracellular matrix proteins of the invention is co-transfected with a gene encoding neomycin resistance. Alternatively, the gene encoding neomycin resistance is physically linked to the sequence encoding the soluble extracellular matrix proteins. Transfection is carried out by any one of several methods well known to those of ordinary skill in the art (E. J. Robertson, supra). Calcium phosphate/ DNA precipitation, direct injection, and electroporation are the preferred methods. Following DNA introduction, cells are fed with selection medium containing 10% fetal bovine serum in DMEM supplemented with G418 (between 200 and 500$\mu$ g/ml biological weight). Colonies of cells resistant to G418 are isolated using cloning rings and expanded. DNA is extracted from drug resistant clones and Southern blotting experiments using a transgene-specific DNA probe are used to identify those clones carrying the sequence(s). In some experiments, PCR methods are used to identify the clones of interest.

DNA molecules introduced into ES cells can also be integrated into the chromosome through the process of homologous recombination. Copecchi, *Science*, 244: 1288–1292 (1989). Direct injection results in a high efficiency of integration. Desired clones are identified through PCR of DNA prepared from pools of injected ES cells. Positive cells within the pools are identified by PCR subsequent to cell cloning. DNA introduction by electroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by Copecchi, supra and Joyner et al., *Nature*, 338:153, 1989, the disclosures of which are incorporated herein.

EMBRYO RECOVERY AND ES CELL INJECTION: Naturally cycling or superovulated female mice mated with males are used to harvest embryos for the implantation of ES cells. It is desirable to use the C57BL165 strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10–20 ES cells are injected into blastocysts using a glass microneedle with an internal diameter of approximately 20 $\mu$m.

TRANSFER OF EMBRYOS TO RECEPTIVE FEMALES: Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

IDENTIFICATION OF TRANSGENIC MICE AND RATS: Tail samples (1–2 cm) are removed from three week old animals. DNA is prepared and analyzed by Southern blot or PCR to detect transgenic founder ($F_0$) animals and their progeny ($F_1$ and $F_2$). In this way, animals that have become transgenic for the sequences encoding soluble extracellular matrix protein are identified. Because not every transgenic animal expresses the soluble extracellular matrix protein, and not all of those that do will have the expression pattern anticipated by the experimenter, it is necessary to characterize each line of transgenic animals with regard to expression of the protein in different tissues.

Production of Non-Rodent Transgenic Animals

Procedures for the production of non-rodent mammals and other animals have been discussed by others. See Houdebine and Chourrout, supra; Pursel et al., *Science* 244:1281, 1989; and Simms et al., *Bio/Technology,* 6:179, 1988.

EQUIVALENTS

It should be understood that the preceding is merely a detailed description of certain preferred embodiments of the present invention. It therefore should be apparent to those skilled in the art that various modifications and equivalents can be made without departing from the spirit or scope of the invention.

What is claimed is:

1. A cosmetic composition comprising:
   a cosmetic carrier; and
   at least two protein isomorphs of tropoelastin, wherein the isomorphs are proteins that were not previously cross-linked and therefore are available for cross-linking and are present in ratios approximately identical to those at which the isomorphs are present in epidermis of a selected human individual.

2. The cosmetic composition of claim 1 wherein at least one of the tropoelastin protein isomorphs has been modified to increase its solubility in aqueous medium.

3. The cosmetic composition of claim 2 wherein the modification comprises addition of a moiety selected from the group consisting of liposomes, fatty acids, carbohydrates, lipids, and proteins.

4. The cosmetic composition of claim 3 wherein the modification comprises addition of amino acids selected from the group consisting of hydrophobic amino acids, hydrophilic amino acids, or lysine-rich amino acids.

5. The cosmetic composition of claim 1 wherein at least one of the tropoelastin protein isomorphs has been modified to reduce its antigenicity.

6. The cosmetic composition of claim 5 wherein the modification comprises alteration of a solvent-accessible portion of the tropoelastin protein isomorphs.

7. The cosmetic composition of claim 1 wherein at least one of the tropoelastin protein isomorphs has been modified to increase its solubility in organic solvents.

8. The cosmetic composition of claim 1 further comprising an agent selected from the group consisting of antibiotics, anti-inflammatories, anesthetics, and combinations thereof.

9. The cosmetic composition of claim 1 further comprising an extracellular matrix component selected from the group consisting of collagen, fibronectin, and laminin.

* * * * *